United States Patent
Bhitiyakul

[11] Patent Number: 6,042,566
[45] Date of Patent: Mar. 28, 2000

[54] INTRAVENOUS INJECTION APPARATUS

[76] Inventor: Somsak Bhitiyakul, 41 Tall Oaks Dr., Kingston, N.Y. 12401

[21] Appl. No.: 09/431,617

[22] Filed: Nov. 2, 1999

Related U.S. Application Data

[63] Continuation of application No. 08/359,567, Dec. 19, 1994.
[51] Int. Cl.[7] .................................................. A61M 5/178
[52] U.S. Cl. ......................... 604/164; 604/167; 604/168
[58] Field of Search .................................. 604/164, 165, 604/167, 168, 191, 197, 256

[56] References Cited

U.S. PATENT DOCUMENTS

| | | | |
|---|---|---|---|
| 4,585,440 | 4/1986 | Tchervenkov et al. | 604/164 |
| 5,743,891 | 4/1998 | Tolkoff et al. | 604/198 |

*Primary Examiner*—Wynn Wood Coggins
*Assistant Examiner*—A. T. Nguyen
*Attorney, Agent, or Firm*—Charles J. Brown

[57] ABSTRACT

In intravenous fluid injection wherein a syringe needle and surrounding sheath are inserted into a vein so that blood flows through the needle into a transparent hollow push-pull element fixed on the needle remote from its point to indicate proper vein insertion, and the needle is then withdrawn from the sheath and from a vial on the end of the sheath through an opening in the vial so that blood back-flows into the vial before intravenous fluid is introduced through the vial and sheath into the vein, apparatus for preventing blood leakage from the vial opening wherein the opening is covered with an elastomeric diaphragm through which the needle is initially pierced and which resiliently self-seals when the needle is withdrawn therefrom, and further wherein intravenous fluid is introduced through a port in the vial separate from the opening covered by the diaphragm, the vial having a substantially fixed volume which remains substantially unchanged during operation, so that upon withdrawal of the needle from the sheath and vial through the vial opening any leakage of blood out of the vial opening is prevented by the diaphragm.

4 Claims, 1 Drawing Sheet

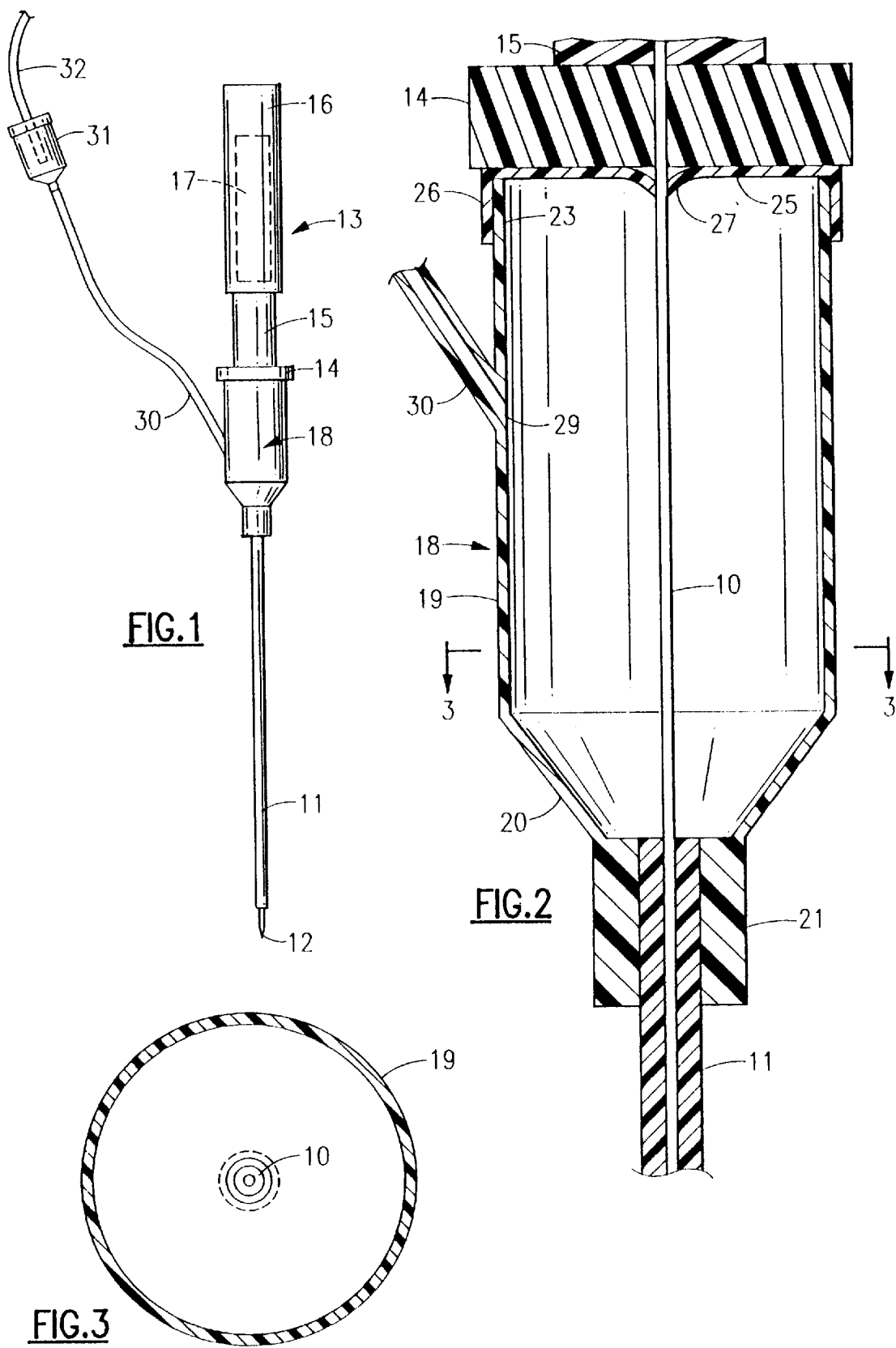

INTRAVENOUS INJECTION APPARATUS

CROSS REFERENCE TO RELATED APPLICATION

This application is a continuation of application Ser. No. 08/359,567, filed Dec. 19, 1994 and entitled "IMPROVED METHOD OF INTRAVENOUS INJECTION AND APPARATUS THEREFOR", now abandoned.

BACKGROUND OF THE INVENTION

Conventional intravenous catheter apparatus includes a hollow syringe needle and a close-fitting surrounding sheath from which a point of the needle initially projects. The needle point and sheath are inserted into a vein so that blood back-flows through the needle into a transparent hollow push-pull element, usually cylindrical and somewhat elongated, fixed on the needle remote from its point. The appearance of blood within that transparent element indicates that the needle and sheath have been properly inserted in the vein. Typically there is a cylindrical elongated vial coaxially located on the end of the sheath and the needle initially extends coaxially through a circular end opening in the vial and through the sheath. After proper insertion in the vein the needle is then withdrawn from the sheath and from the vial through the opening in the vial and is discarded. The end of a flexible tube is then fitted into the vial opening to communicate with a source of intravenous fluid.

It is common in this prior art method of intravenous injection to experience leakage of blood between the time that the needle is withdrawn from the vial opening and the intravenous connector tube is inserted in the vial opening. The person performing the procedure must pull the needle from the sheath and vial with one hand and discard it while keeping the sheath properly in place in the vein by holding the vial on the sheath with the other hand. During that interim blood back-flows outwardly from the vein through the sheath into the vial and thence through the vial opening. It is the principal purpose of the present invention to modify this conventional method of intravenous injection and apparatus therefor so that blood back-flowing into the vial after the needle is removed cannot proceed further and all leakage of blood from the vial prior to introduction of the intravenous fluid is prevented.

Some but certainly not all of the components of the catheter of the present invention which achieve this purpose are disclosed in my prior Pat. No. Design 336,334 issued Jun. 8, 1993. It will be seen from the description below that use of a self-sealing pierced elastomeric diaphragm is part of the present solution in achieving these objectives. Self-sealing elements as such are known in the medical field, as for example the hemostasis valve described in U.S. Pat. No. 4,626,245 and the pierced resealable seal described in U.S. Pat. No. 4,950,260. Neither of those references, however, and as far as is known no other prior art references, disclose the use of a pierced resealable elastomeric diaphragm in conjunction with a needle on a transparent intravenous push-pull element with the diaphragm located over an opening in an intravenous vial and with a vial port separate from that vial opening for connection to a source of intravenous fluid. A side port is associated with the resealable valve of U.S. Pat. No. 4,626,245 but not for introduction of intravenous fluid. This is true also of a side port described in U.S. Pat. No. 5,021,044.

SUMMARY OF THE INVENTION

The invention provides an intravenous catheter which includes a syringe needle slidable within a sheath from one end of which a point on the needle initially projects. A transparent hollow push-pull element is located on the needle end remote from its point to receive blood through the needle to indicate proper vein insertion. On the end of the sheath opposite the needle point is an intravenous fluid-receiving vial. The needle initially extends through an opening in the vial and through the vial and sheath. The improved apparatus for preventing blood leakage from the vial opening comprises an elastomeric diaphragm covering the vial opening through which the needle is initially pierced and which resiliently self-seals when the needle is withdrawn therefrom. The vial has a substantially fixed volume which remains substantially unchanged during operation. An intravenous fluid-receiving port is included in the vial separate from the opening covered by the diaphragm. Upon insertion of the needle and sheath into a vein and the appearance of blood in the transparent push-pull element followed by withdrawal of the needle from the sheath and from the vial opening, blood is prevented from leaking through the vial opening by the diaphragm and intravenous fluid is introduced through the separate vial port.

In a preferred form of the apparatus of the invention the vial is elongated, the vial opening covered by the diaphragm is located on the end of the vial opposite the sheath and the separate port is located on the side of the vial. The vial may be cylindrical, the vial opening may then be circular and both may be substantially coaxial with the sheath. In that case the diaphragm is initially pierced by the needle at the center of the vial opening. A flexible tube may be affixed to the vial extending from the port to a connector adapted to communicate with a source of intravenous fluid.

BRIEF DESCRIPTION OF THE DRAWINGS

FIG. 1 is an overall view of the improved catheter of the invention;

FIG. 2 is an enlarged longitudinal fragmentary section principally of the vial of the catheter; and FIG. 3 is an enlarged cross section taken along the line 3—3 of FIG. 2.

DESCRIPTION OF PREFERRED EMBODIMENT

Referring to FIGS. 1 to 3 a hollow metal syringe needle 10 is closely surrounded by a plastic sheath 11 so that a pointed end 12 of the needle 10 initially projects slightly from the end of the sheath 11. Since the needle 10 and surrounding sheath 11 are to be inserted into a vein the end of the sheath 11 adjacent then projecting pointed end 12 of the needle 10 may be faired around the needle so as to minimize a sheath edge which might interfere with such insertion. An elongated transparent hollow push-pull element 13 is fixed on the needle end remote from its point 12. The push-pull element includes a circular flange 14 which appears in FIG. 2, a cylindrical central section 15 and a cylindrical transparent hollow end portion 16 adapted to be grasped by the fingers of the nurse or doctor. Within the transparent end portion 16 is a chamber 17 into which the interior of the needle 10 communicates. When the needle and surrounding sheath are inserted into a vein, blood flows through the needle 10 into the chamber 17 in the transparent end portion 16 to indicate proper vein insertion. The push-pull element 13 and its component parts comprising the flange 14, the central section 15 and the end portion 16 are of unitary molded plastic construction.

On the end of the sheath 11 remote from the point 12 of the needle 10 is a cylindrical vial 18 shown in detail in FIGS. 2 and 3. It includes a cylindrical body 19, a funnel portion 20 converging to a ferrule portion 21 surrounding the end of the sheath 11. There is a circular opening in the vial 19 at the end of the body portion remote from the funnel portion 20 defined by a circumferential body end portion 23. The vial 19 has a substantially fixed volume which remains substantially unchanged during operation. In prior art methods and catheter designs the needle 10 is withdrawn from the sheath 11 and from the vial 18 through the opening defined by the vial body end portion 23 and is discarded. The nurse or doctor holds the push-pull element 13 with the fingers of one hand to pull the needle 11 out while grasping the vial 18 with the fingers of the other hand to keep the sheath 11 in place in the vein. The next step in this prior art practice is to insert the end of an intravenous fluid tube into the circular opening in the vial body 18 defined by the end portion 23. In the interim blood back-flows through the sheath 11 into the vial 18 and can leak outwardly through the opening defined by the vial body end portion 23 before the intravenous tube can be connected.

The apparatus of the invention for preventing such blood leakage from the vial opening comprises covering the vial opening with a circular elastomeric diaphragm 25 having a rim 26 which fits about the end portion 23 of the vial body 18 and may be glued in place. In the assembly of the apparatus the needle 10 is factory-fitted through the center of the diaphragm 25 by piercing the diaphragm to form a hole in the diaphragm which is defined by an encircling lip 27 resiliently gripping the needle 10. When the needle 10 is withdrawn from the diaphragm 25 the encircling lip 27 contracts resiliently to eliminate the hole in a self-sealing fashion. Any blood which flows into the vial 18 after the needle 10 is withdrawn is prevented from leaking out of the vial by the diaphragm 25.

Since the circular end opening in the vial body 19 defined by the end portion 23 is permanently closed by the diaphragm 25 it is not possible to insert the end of an intravenous tube into that opening to introduce intravenous fluid through the vial 18 and sheath 11 into the vein. Therefore a port 29 separate form the opening covered by the diaphragm 25 is provided in the vial 18 preferably in the cylindrical side of the vial body portion 19 as shown in FIG. 2. The end of a flexible tube 30 is permanently inserted in the port 29 and at its remote end a conventional intravenous a connector 31 is provided for selective connection with a tube 32 leading to a source of intravenous fluid.

In the operation of the catheter of the invention, the parts are preassembled in the factory as shown in FIG. 1 with the pointed end 12 of the needle 10 projecting slightly from the end of the sheath 11. The flange portion 14 of the push-pull element 13 at this point is flush against the outside of the diaphragm 25 as shown in FIG. 2. The nurse or doctor grasps the vial 18 and push-pull element 13 with the fingers of one hand and inserts the end of the needle 10 and sheath 11 into the patient's vein. As a consequence blood back-flows out through the interior of the needle 10 and into the chamber 17 in the transparent end portion 16 of the push-pull element 13. The appearance of blood in the chamber 17 indicates that the needle and sheath are properly in place in the vein. The nurse or doctor then grasps the vial 18 with the fingers of one hand and the push-pull element 13 with the fingers of the other hand and pulls the push-pull element 13 out so that the needle 10 is withdrawn out of the sheath 11 and vial 18 and finally out of the central pierced hole in the diaphragm 25. That hole instantly closes as the lip 27 contracts resiliently.

The used push-pull element 13 and needle 10 are then discarded but while that is happening blood is entering the vial 18 through the sheath 11. However it is prevented from leaking out of the vial 18 by the diaphragm 25. The connector 31 may have been preconnected to the tube 32 leading to a source of intravenous fluid or the connector 31 may be so connected after the push-pull element 13 and needle 10 are discarded, but in any case the making of that connection prevents leakage of blood through the flexible tube 30. When the intravenous fluid source is opened the fluid flows through the flexible tube 30, into the vial 18 and then through the sheath 11 into the patient's vein.

The scope of the invention is to be determined form the following claims rather than the foregoing description of a preferred embodiment of the invention.

What is claimed is:

1. In a combination an intravenous catheter wherein a syringe needle is slidable within a sheath from one end of which a point on the needle initially projects, a transparent hollow push-pull element is on the needle end remote from its point to receive blood through the needle to indicate proper vein insertion and an intravenous fluid-receiving vial is on the end of the sheath opposite the needle point, the needle initially extending through an opening in the vial and through the vial and sheath, means for preventing blood leakage from the vial opening comprising a) an elastomeric diaphragm covering the vial opening through which the needle is initially pierced and which resiliently self-seals when the needle is withdrawn therefrom, b) said vial having a substantially fixed volume which remains substantially unchanged during operation, c) an intravenous fluid-receiving port in the vial separate from the opening covered by the diaphragm, d) whereby upon insertion of the needle and sheath into a vein and the appearance of blood in the transparent push-pull element followed by withdrawal of the needle from the sheath and vial opening blood is prevented from leaking through the vial opening by the diaphragm and intravenous fluid is introduced through the separate vial port.

2. An intravenous catheter according claim 1 wherein the vial is elongated, the vial opening covered by the diaphragm is located at an end of the vial opposite the sheath and the separate port is located on the side of the vial.

3. An intravenous catheter according to claim 2 wherein the vial is cylindrical, the vial opening is circular and both are substantially coaxial with the sheath, and the diaphragm is pierced at the center of the vial opening.

4. An intravenous catheter according to claim 1 wherein a flexible tube is affixed to the vial extending from the port to a connector adapted to communicate with a source of intravenous fluid.

\* \* \* \* \*